(12) United States Patent
Hendrich et al.

(10) Patent No.: US 7,140,259 B2
(45) Date of Patent: Nov. 28, 2006

(54) EXPANDED PLUG METHOD FOR DEVELOPING CIRCUMFERENTIAL MECHANICAL PROPERTIES OF TUBULAR MATERIALS

(75) Inventors: William Ray Hendrich, Oak Ridge, TN (US); Wallace Jefferson McAfee, Oak Ridge, TN (US); Claire Roberta Luttrell, Oak Ridge, TN (US)

(73) Assignee: U. T. Battelle, LLC, Oak Ridge, TN (US)

( * ) Notice: Subject to any disclaimer, the term of this patent is extended or adjusted under 35 U.S.C. 154(b) by 84 days.

(21) Appl. No.: 10/952,503

(22) Filed: Sep. 28, 2004

(65) Prior Publication Data

US 2006/0070455 A1  Apr. 6, 2006

(51) Int. Cl.
 *G01N 3/08* (2006.01)
(52) U.S. Cl. ........................................ 73/824
(58) Field of Classification Search .................. 73/824
 See application file for complete search history.

(56) References Cited

U.S. PATENT DOCUMENTS 4,004,972 A  1/1977  Mogard
4,785,675 A * 11/1988 Takasu et al. ......... 73/862.325
4,822,559 A  4/1989  Mogard

OTHER PUBLICATIONS

Daum et al., "Mechanical Properties of Irradiated Zircaloy—4 for Dry Cask Storage Conditions and Accidents" *Nuclear Safety Research Conference*, Washington DC (2003).
Daum et al. Mechanical Property Testing of Irradiated Zircalog Cladding Under Reactor Transient Conditions,:*Small Specimen Test Techniques: Fourth Volume*, ASTM STP 1418, M A Solokov, JD Landes and G E Lucas eds. ASTM West Conshohockey PA (2002) and Link et al., Nuclear Engineering and Design, 186, 379 (1998).
S. Uchikawa, "Ring Tinsile Testing of Zircaloy Cladding Tubes at JAERI" *FSRM*, Tokyo (2004) and ASTM D 2290-92 (1992).
Dufoumeaud et al, "Elastic-Plastic Deformation of a Nuclear Fuel Cladding Specimen Under the Internal Pressure of a Polymer Pellet" *World Congress on Computational Mechanics*, Vienna (2002).

* cited by examiner

*Primary Examiner*—Max Noori
(74) *Attorney, Agent, or Firm*—J. Herbert O'Toole; Nexsen Pruet, LLC

(57) ABSTRACT

A method for determining the circumferential properties of a tubular product, especially nuclear fuel cladding, utilizes compression of a polymeric plug within the tubular product to determine strain stress, yield stress and other properties. The process is especially useful in the determination of aging properties such as fuel rod embrittlement after long burn-down.

7 Claims, 3 Drawing Sheets

EXPANDED PLUG METHOD FOR DEVELOPING CIRCUMFERENTIAL MECHANICAL PROPERTIES OF TUBULAR MATERIALS

STATEMENT OF U.S. GOVERNMENT RIGHTS

This invention was made with United States Government support under Contract No. DE-AC05-96OR22725 between the United States Department of Energy and UT-BATTELLE, LLC, and the United States Government has certain rights in this invention.

FIELD OF THE INVENTION

The invention relates to a destructive testing method for determining circumferential mechanical properties of tubular products by applying a mechanical, radial uniform pressure from the inside of the tubular product.

BACKGROUND OF THE INVENTION

The testing of tensile strength and bursting strength of tubular products presents difficulties due to the number of types, sizes and uses for tubing. High temperature and pressure, usually with corrosion and shock loading, are problems in transportation, power generation, petrochemical systems. A particular concern is the cladding for fuel rods in nuclear power reactors including the many light water reactors used in Western countries.

The preferred material for nuclear fuel rod cladding in light water reactors is currently Zircaloy-4, manufactured by Sandvik Special Metals Corporation, Division of Sandvik Nuclear AB, Nykoping, SE. The basic design consideration in fuel rod designs are succinctly described in U.S. Pat. No. 4,004,972 to Mogard and in U.S. Pat. No. 4,822,557, also to Mogard. The discussions therein refer to conventional fuels at low burn-up (e.g., less than 60 GWd/MTU). Higher burn-up rates are desirable for lower net fuel costs. MOX (mixed uranium oxide, weapons grade plutonium oxide) is contemplated in the future for the disposal of surplus weapons grade plutonium, and its use entails both engineering and political questions.

Mechanical testing of fuel rod cladding using axial and circumferential load tests have been reported by R. S. Daum et at, "Mechanical Properties of Irradiated Zircaloy-4 for Dry Cask Storage Conditions and Accidents" *Nuclear Safety Research Conference*, Washington D.C. (2003), R. S. Daum et al., "Mechanical Property Testing of Irradiated Zircalog Cladding Under Reactor Transient Conditions," *Small Specimen Test Techniques: Fourth Volume*, ASTM STP 1418, M. A. Solokov, J. D. Landes and G. E. Lucas eds, ASTM, West Conshohockey Pa. (2002), and Link et al., Nuclear Engineering and Design, 186, 379 (1998).

Methods using split rings to apply radial pressure include S. Uchikawa, "Ring Tensile Testing of Zircaloy Cladding Tubes at JAERT," FSRM, Tokyo (2004) and ASTM D 2290-92 (1992). A test described as Expansion Due to Compression Test was reported by Dufourneaud et al., *World Congress on Computational Mechanics*, Vienna (2002) uses a polymer pellet axially compressed inside a tube by two pistons pressing at opposite sides.

The U.S. Department of Energy (DOE) Fissile Materials Disposition Program (FMDP) is pursuing reactor irradiation of mixed uranium-plutonium oxide (MOX) fuel for disposal of surplus weapons-usable plutonium. To pursue disposition of surplus weapons-usable plutonium via reactor irradiation, it must be demonstrated that the unique properties of the surplus weapons-derived or weapons-grade (WG) plutonium do not compromise the applicability of this MOX experience base.

One question to be addressed for weapons-derived MOX fuel is that of ductility loss of the cladding during irradiation. While irradiation induced loss of ductility has long been known and quantified for many cladding materials, the potential synergistic effects of irradiation and the unique constituents (i.e., gallium) of weapons-derived MOX fuel are not known. The Postirradiation Clad Ductility test Program formulated for DOE is conducted by the Oak Ridge National Laboratory (ORNL). The program focus is on development, validation, and application of technology for the determination of the residual ductility for mixed oxide (MOX) fuel cladding irradiated in the Advanced Test Reactor (ATR). The scope of the project includes development of techniques for machining and handling of small ring-type test specimens, development and validation of a specimen and test fixture for use in a hot cell environment, and testing of cladding specimens subjected to burnup levels from zero to more than 50 GWd/MT.

The test methods described above (e.g. ASTM D 2290–92) are applicable to clean rods and samples which have been scrupulously cleaned. They are bench tests and not safe or suitable for routine, reliable data collection in a hot cell environment where manipulation is limited.

BRIEF DESCRIPTION OF THE INVENTION

A method for testing fuel rod cladding ductility in a hot cell utilizes an expandable plug to stretch a small ring of the irradiated cladding material. The specimen strain is determined using the measured diametrical expansion of the ring. This method removes many complexities associated with specimen preparation and testing. The advantages are simplicity of test component assembly in the hot cell and the direct measurement of specimen strain. It was also found that cladding strength could be determined from the test results.

A slice of fuel rod cladding is cut off within a hot cell. The slice specimen is mounted over a polymeric plug, The polymeric plug has an alignment dowel that is inserted into a support post that forms the lower end of the test fixture. A ram compresses the plug from above and the distortion/expansion of the specimen is measured by non-contact means such as proximity transducers. Installation of the specimen is through manipulators, and control of all equipment is from outside the hot cell using remote electrical connections. Virgin samples and tested samples are passed into and out of the hot cell through an air lock.

DETAILED DESCRIPTION OF THE INVENTION

A simple test has been developed to determine the ductility of irradiated cladding of weapons-derived MOX test fuel. While the anticipated range of applicability for this test method is for measurement of cladding ductility (as indicated by circumferential strain) in the range of 1–5 percent, circumferential strain in excess of 15 percent has been induced in test samples of unirradiated Zircaloy-4.

The current test technique utilizes a 7.137-mm (0.281-in.) long ring of cladding that is expanded radially by applying an axial compressive load to a cylindrical plug of polyurethane fitted inside the specimen.

Short lengths ranging from 40.6-mm to 132.1-mm (1.6-in. to 5.2-in) are used in to the cladding ductility investigation for preparation of specimens. To meet the dimensional and perpendicularity requirements of the specimens, and adhering to the remote operations and simplicity needs of the specimen preparation, a saw with a precision diamond wafering blade was used to cut specimens. A Buehler Isomet 5000 cut-off saw was selected as best fitting the requirements. This is a wet saw where translation of the saw blade in its plane and positioning of the work piece perpendicular to the saw plane are motor driven and computer controlled operations. The machine itself is computer controlled and programmable for cutting speed, material movement, number of specimens cut, etc., and can be controlled from outside the hot cell.

Provision for de-burring of the clad samples, if required, is also included in the saw equipment. After the ring specimens are cut and de-burred, they are stored in previously marked individual containers, which are inserted into lead pigs using remote manipulators.

Figure 1:
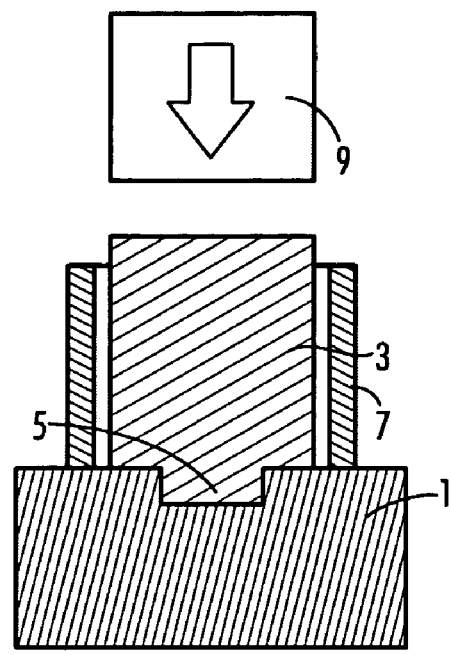
FIG. 1 is a schematic drawing of the test concept of this invention.

A schematic of the test concept is shown in FIG. 1. A stage 1 (support post) is firmly mounted to the lower crosshead of a test machine (not shown). A polyurethane plug 3, preferably having a dowel end 5 is inserted into the top of the stage. The specimen 7 is placed around the plug and a loading ram 9 compresses the plug.

Figure 2:
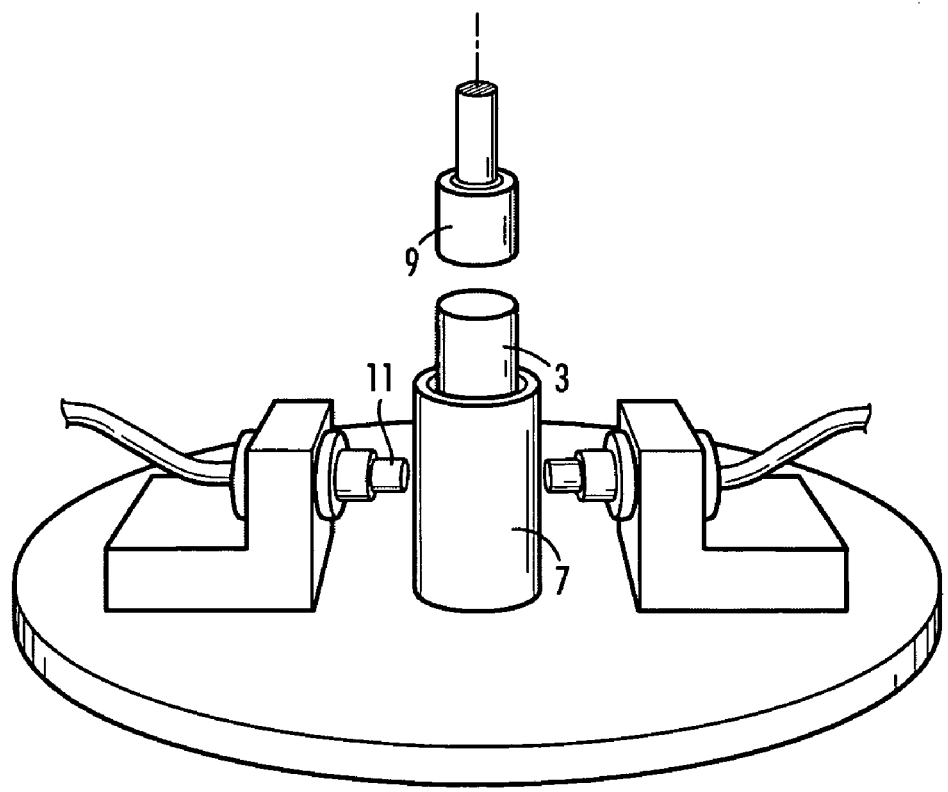
FIG. 2 illustrates the location of proximity transducers relative to the specimen

The preferred plug material is polyurethane with a hardness of Shore A=95. As the loading ram compresses the plug, the plug undergoes radial expansion, which in turn expands the specimen. The increase in diameter of the specimen is continuously monitored and recorded using non-contacting proximity transducers 11 as is shown in FIG. 2. The diameter increase of the specimen is used to calculate the circumferential strain accrued during the test.

The test load was applied with a Materials Test Systems (MTS) Alliance RT/50 screw driven ram test machine. This machine has a maximum load capacity of 50-kN (11,250 lbf). A screw driven machine is preferred over servo-hydraulic machines to minimize the potential for release of chemical containments into the hot cell in the case of machine seal failure. The machine is computer controlled using a software set-up to control the complete test histogram as well as to record all data.

As the ram compresses the plug, the plug undergoes radial expansion, which in turn expands the specimen. A dowel 5 at the lower end of the plug was found to be helpful for alignment during set-up and to control the expansion of the plug bottom. The increase in diameter of the specimen is continuously monitored and recorded using non-contacting proximity transducers (Capacitec—Ayer Mass. US) as shown in FIG. 2. The diameter increase of the specimen is used to calculate the circumferential strain accrued during the test. Only two diametrically opposed transducers are needed since post-test measurements of deformed specimens showed that radial expansion was uniform until localized failure of the specimen occurred.

During testing, the machine crosshead moves the ram downward until it comes into contact with the upper end of the plug. As the ram continues to move downward it compresses the plug, which undergoes radial expansion. As the plug expands, it contacts and expands the specimen as a result of internal pressure. The dowel at the lower end of the plug serves a very important function during the deformation process. First, it serves to hold the specimen assembly in proper alignment as the plug is compressed. Second, it controls expansion of the lower end of the plug, which is beneficial in achieving uniform expansion along the plug length. The increase in diameter of the specimen is continuously monitored and recorded using the non-contacting Capacitec proximity transducers. The diameter increase of the specimen is used to calculate the circumferential strain accrued during the test. Only two diametrically opposed transducers are required since post-test measurements of deformed specimens have shown that radial expansion is uniform until the initiation of localized failure. A scale parameter (Γ-Factor) is used to convert load to stress for the test setup as shown below:

Let (1)
$$\sigma = \Gamma \frac{P}{tl} = \text{circumferential stress in specimen.}$$

Then, (2)
$$\Gamma = \frac{\sigma_{yield}}{P_{yield}} tl,$$

where
Γ=scale parameter,
$\sigma_{yield}$=material yield strength as measured in ASTM type tensile test,
$P_{yield}$=load at 0.2 percent plastic strain measured in expanded-plug loading test,
t=ring specimen wall thickness, and
l=ring specimen axial length.

This scale parameter is developed by normalizing the yield load in the ring test (yield load is defined as the load at which the specimen has undergone 0.002 in/in of circumferential plastic strain) to the yield stress measure in a conventional tensile test of the same material. Once the σ-Factor is quantified using a known material, it is a constant for the same expanded-plug setup, i.e., the same specimen size, the same plug size and material, the same temperature, and the same loading rate. It is not related specifically to the material being tested, but is a function of the technique. The value of σ can be taken as a constant for a particular test set-up and can be applied to test data from other materials tested using this set-up. The validity of this approach has been verified by testing on several different materials. The total load applied to the test assembly goes into compressing the plug and stretching the ring specimen. The stiffness of the plug is easily measured by simply running a compression test of the plug alone. A correlation can then be developed between measured plug compression and the load applied to the plug. For a specimen test, use of this correlation allows separation of the plug load and specimen load, which makes the final test results independent of plug properties.

While this test has been developed for an unique application, it can be applied to a range of materials and tubular product sizes by simple modification of the test setup and re-calculation of the σ-Factor.

Figure 3:
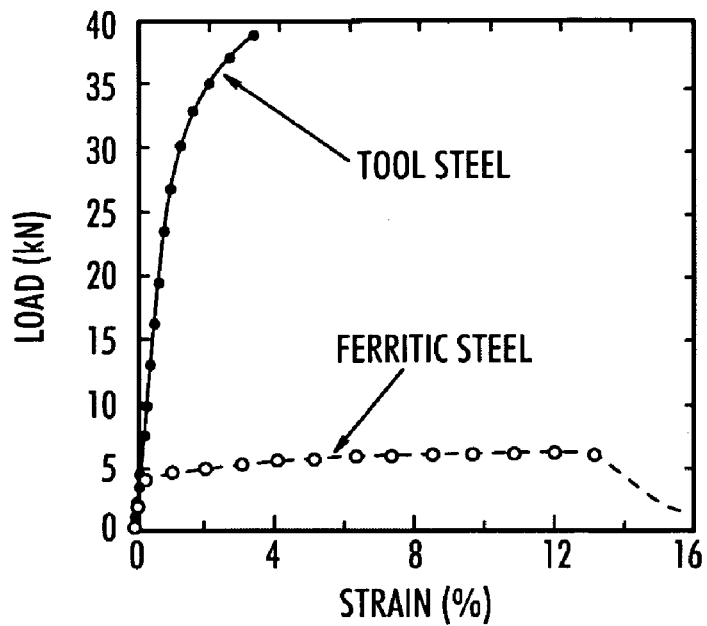
FIG. 3 shows load/strain plots for tool steel and ferritic steel.

To validate the approach, specimens of highly divergent strengths and ductilities were tested. FIG. 3 shows test results for head-treated tool steel [ultimate strength 2.1 Gpa (305 ksi)] and an intermediate strength ferritic steel [ultimate strength 0.6 GPa (87 ksi)]. The two steels were chosen to bracket the expected results from Zircaloy-4.

Experimental

Figure 4:
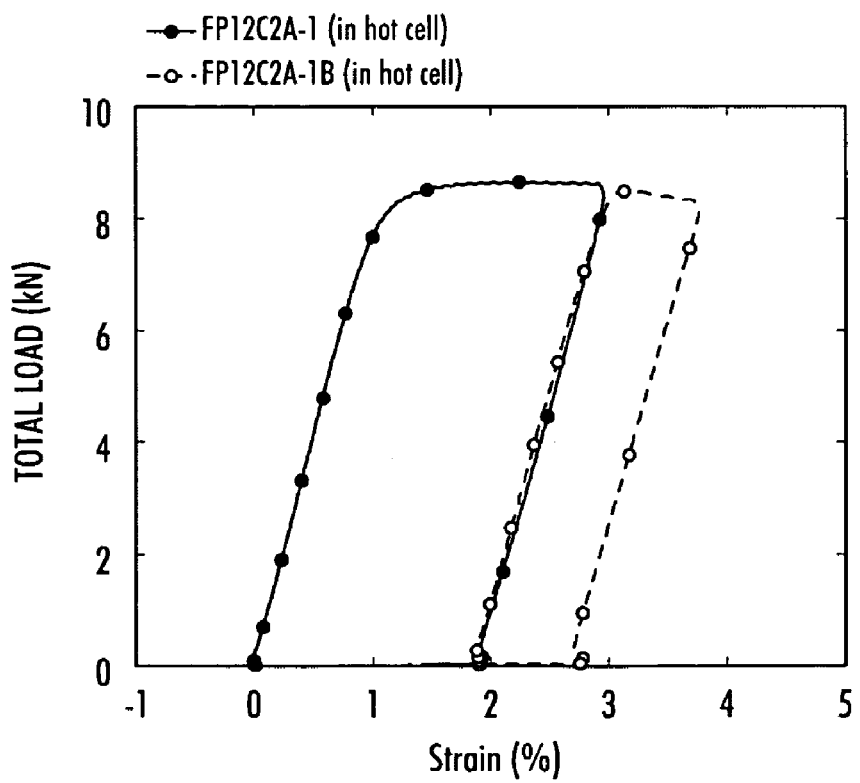
FIG. 4 shows load/strain plot for irradiated cladding sample FP12C2A-1 and FP12CA-1B in a hot cell.

The first irradiated specimen, FP12C2A-1, was strained monotonically to a maximum strain of 2.9 percent and unloaded as shown in FIG. 4. Examination of the data showed that, in the elastic regime, the strain rate was approximately 0.008 mm/mm/min. A standard ASTM tensile test would be run at approximately 0.010 mm/mm/min. The strain rate in the plastic regime was about 0.043 mm/mm/min. This marked increase in the plastic region is due to the fact that the machine crosshead moves at a constant rate throughout the test.

Figure 5:
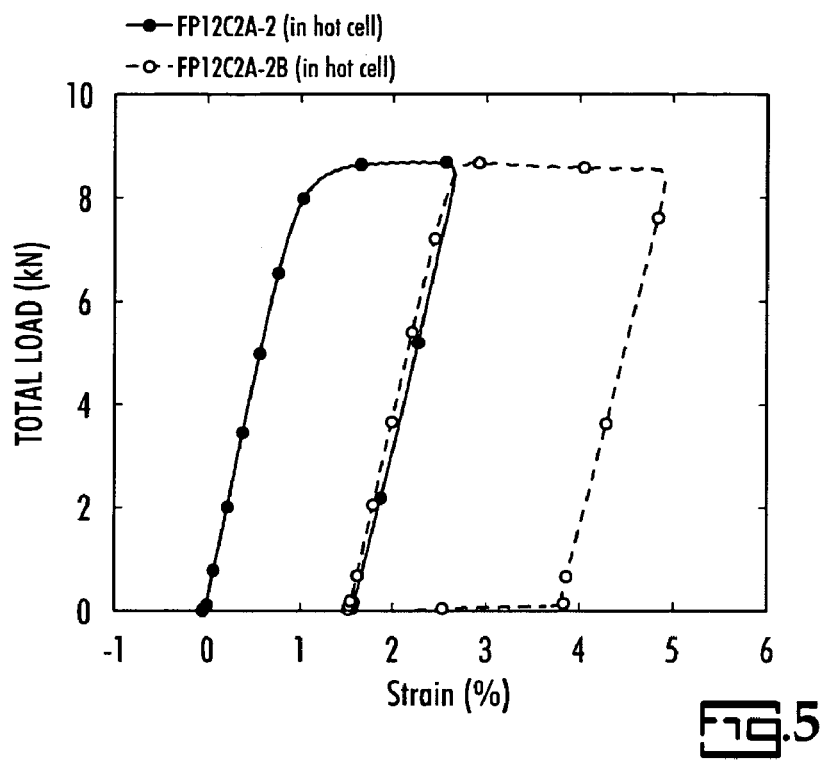
FIG. 5 shows a load//strain plot for irradiated cladding, sample FP 12C2A-2 and FP12C2A-2B.

The deformation plot at the date acquisition monitor indicated that the specimen load peaked before the maximum strain was reached, i.e., that the specimen had gone through ultimate load (FIG. 5). It was thus decided to perform a re-test and increase the applied strain to verify that maximum load was exceeded. The results are shown in FIG. 4 as Specimen FP12C2A-1B. It was evident from this re-test that ultimate load had been exceeded and that the specimen was in the plastic collapse portion of the histogram. This re-load took the specimen to 3.9 percent total strain.

The second irradiated specimen, FP12C2A-2 was tested to a maximum strain of 2.2 percent before unload. It was then also re-tested. The results showed that, on the re-load, after reaching maximum load under basically elastic strain, the load immediately began to drop. This confirmed that the ultimate load had been exceeded on the initial load-up. Adding the permanent strain measured in the initial load cycle to that measured in the re-load approximated the total strain for the combined test and re-test. The specimen total strain was then estimated to be 4.9 percent.

The re-load for Specimen FP12C2A-2 (B) demonstrates the consistency of this test technique. The reload strain was indexed to the maximum permanent strain measured in the initial load cycle. The re-load elastic line then traces the unload portion of the initial load cycle picking up the inelastic response (magnitude, slope) as almost an exact continuation of the initial loading cycle.

The results of greatest interest for the MOX Demonstration Tests are summarized in uniform elongation. For comparison, Zr-4 cladding irradiated in the absence of hydrides to fast fluence levels in the range of $7 \times 10^{20}$ n/cm$^2$ to $10^{22}$ n/cm$^2$ (E>1 MeV) has total measured elongations from 2.7 to 4.5 percent. All of the irradiated specimens were tested to strain levels beyond the ultimate strength (uniform elongation) although no failures were recorded. Table 1 includes estimates of the stress levels in the specimens. These were developed using the method discussed above.

These tests have demonstrated the feasibility of the Expanded Plug tensile test method for measuring cladding hoop tensile properties in a hot cell. The technique, which has been developed for MOX cladding, is applicable to thin sections of all low ductility materials. For ductile materials, the strain measurements are correct, but calculation of wall stress will be unreliable at high strain levels.

INDUSTRIAL UTILITY

The process of this invention can be used to test new tubing and pipe and to test for fatigue and embrittlement after use for recertification of nuclear reactors, maritime plumbing and coal-fired power plant steam circuits.

The invention has been described in terms of specific embodiments which demonstrate its novelty and utility. Modifications and adaptations apparent to one with skill in the art are subsumed within the scope of the invention as further recited in the claims.

We claim:

1. A method for determining circumferential mechanical properties of tubular products comprising:
   a) obtaining a representative sample of a tubular product;
   b) placing said representative sample over a polymeric plug having substantially the same height as said representative sample, said polymeric plug being mounted to a fixed surface;
   c) compressing said polymeric plug from above in steps to circumferentially stress said representative sample using a ram and measuring the compressive force applied at each step of its application;
   d) measuring the changes in circumference of said representative sample at each step by measuring the

TABLE 1

| Specimen Number | Maximum Ring Load [lbs(kN)] | Maximum Ring Stress[1] [ksi(MPa)] | Estimated Yield Stress[1] [ksi(MPa)] | Uniform Elongation[2] (%) | Maximum Elongation in Test[3] (%) |
|---|---|---|---|---|---|
| BLGSHC01 | 1521.1(6.77) | 110.8(763.9) | 96.0(661.9) | NA[4] | 3.95 |
| BLGSHC02 | 1529.9(6.81) | 111.5(768.8) | 95.1(655.7) | NA[4] | 3.91 |
| BLGSHC03 | 1528.3(6.80) | 111.4(768.1) | 96.6(666.0) | NA[4] | 4.30 |
| FP12C2A-1 | 1867.6(8.31) | 136.1(938.4)[5] | 130.6(900.5) | 2.03 | 3.93[6] |
| FP12C2A-2 | 1863.5(8.29) | 135.8(936.3)[5] | 128.8(888.0) | 2.20 | 3.35[6] |
| FP12C2A-3 | 1848.4(8.23) | 134.7(928.7)[5] | 128.1(883.2) | 2.19 | 4.18 |

[1]Estimate using Γ -scaling method based on 0.2 percent plastic strain.
[2]Strain at peak load.
[3]Strain at end of test, not failure strain.
[4]Ultimate load no reached.
[5]Material Ultimate Stress.
[6]Obtained on re-load.

Figure 6:
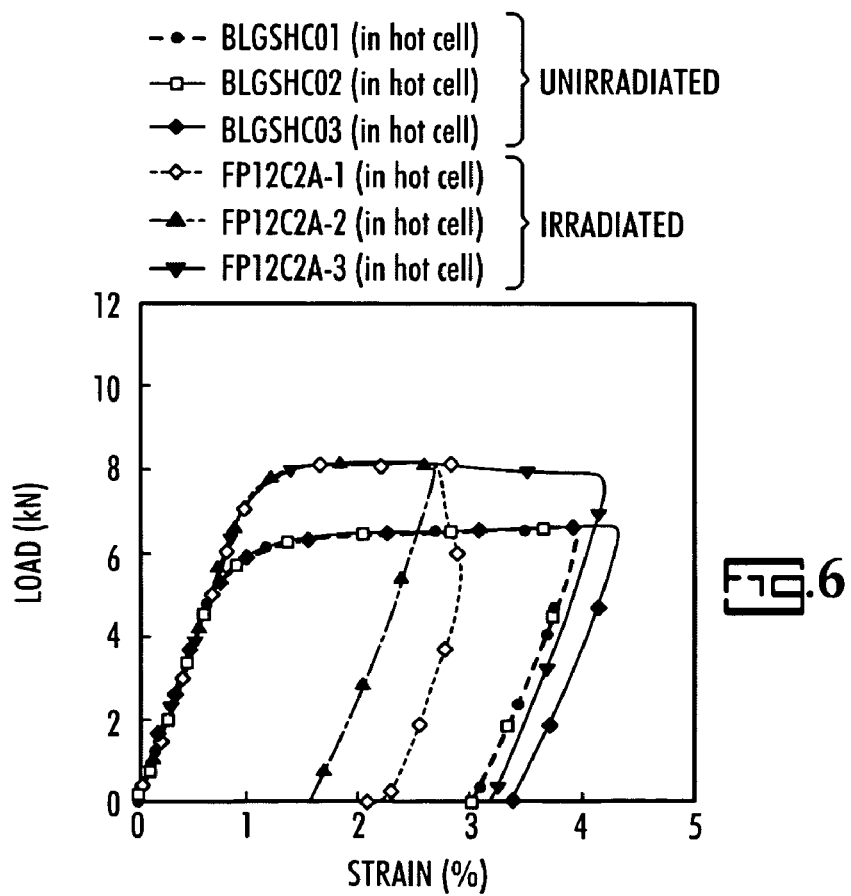
FIG. 6 is a graphical comparison of data from Table 1.

This table is a comparison of the unirradiated and irradiated Zr-4 specimens tested in the hot cell. A graphical comparison of the tabulated Load-Strain results for these specimens is shown in FIG. 6. The effects of irradiation are immediately apparent, i.e., an increase in tensile strength and a substantial decrease in tensile ductility as measured by changes in the diameter of said representative sample using a non-contact method of measurement;
   e) determining the strain of the representative sample of each step of stress force applied; and
   f) calculating a mechanical property of the stressed representative sample.

2. A method according to claim 1 wherein said polymeric plug is a polyurethane plug.

3. A method according to claim 1 wherein the mechanical property determined is maximum ring stress.

4. A method according to claim 1 wherein the mechanical property determined is yield stress.

5. A method according to claim 1 wherein the tubular product is a nuclear fuel rod and the method is performed in a hot cell.

6. A method of determining changes in circumference of a tubular nuclear fuel rod, comprising:
   a) proving a support with a flat surface,
   b) obtaining a representative sample length of said fuel rod,
   c) obtaining a cylindrical polymeric plug of approximately the same length as said sample of said fuel rod and placing it in an upright position on said flat surface,
   d) placing said sample length of said fuel rod over said plug,
   e) axially compressing said polymeric plug in steps using a ram and measuring the compressive force applied at each of said steps,
   f) determining the change in circumference of said sample of said fuel rod by measuring its diameter changes at each of said steps using a pair of non-contact position sensors on diametrically opposite sides of said sample of said fuel rod,
   g) determining the strain of said representative sample at each of said steps of the applied compressive force, and
   h) calculating a mechanical property of the stressed representative sample.

7. The method of claim 6 wherein said support includes a socket and said plug includes a dowel at its lower end which is inserted into said socket when said plug is placed on said flat surface.

* * * * *